United States Patent
Sephus

(10) Patent No.: US 6,589,196 B1
(45) Date of Patent: Jul. 8, 2003

(54) CLEANING KIT FOR OLD PIERCED HOLES IN A PERSON'S BODY

(76) Inventor: Mordena P. Sephus, 13918 S. Avers, Robbins, IL (US) 60472

( * ) Notice: Subject to any disclaimer, the term of this patent is extended or adjusted under 35 U.S.C. 154(b) by 8 days.

(21) Appl. No.: 09/833,424

(22) Filed: Apr. 12, 2001

(51) Int. Cl.$^7$ .................. A61M 35/00; A61M 1/30; A61F 11/00; A61F 9/00
(52) U.S. Cl. .................. 604/1; 604/19; 606/162
(58) Field of Search ............... 604/19, 93.01, 604/164.08, 192, 257, 259, 263, 1, 2, 3; 606/162

(56) References Cited

U.S. PATENT DOCUMENTS

| | | | |
|---|---|---|---|
| 4,041,946 A | * | 8/1977 | Barton .................. 128/260 |
| 4,497,402 A | * | 2/1985 | Karos .................. 206/210 |
| 4,636,203 A | | 1/1987 | Emanis et al. |
| 4,798,216 A | | 1/1989 | Mccarty et al. |
| 5,183,461 A | | 2/1993 | Hobbs |
| D346,443 S | | 4/1994 | Franklin |
| 5,302,043 A | * | 4/1994 | Velliquette .................. 401/208 |
| 5,739,168 A | | 4/1998 | Kioki et al. |
| D401,326 S | | 11/1998 | Powell et al. |
| 6,146,398 A | * | 11/2000 | Satterfield .................. 606/162 |
| 6,248,085 B1 | * | 6/2001 | Scholz et al. .................. 604/2 |
| 6,312,157 B1 | * | 11/2001 | Masuda et al. .................. 383/98 |
| 6,358,221 B1 | * | 3/2002 | Waters et al. .................. 604/1 |

* cited by examiner

Primary Examiner—Edward K. Look
Assistant Examiner—John K Fristoe, Jr.

(57) ABSTRACT

A cleaning kit for old pierced holes in a person's body for cleaning and sanitizing pierced holes of a person's body. The cleaning kit for old pierced holes in a person's body includes a plurality of elongate flexible cleaning members being adapted to pass through pierced holes of a person's body; and also includes a packet member for storing the elongate flexible cleaning members therein; and further includes a container of cleaning solution with the cleaning solution being disposable upon the elongate flexible cleaning members.

5 Claims, 2 Drawing Sheets

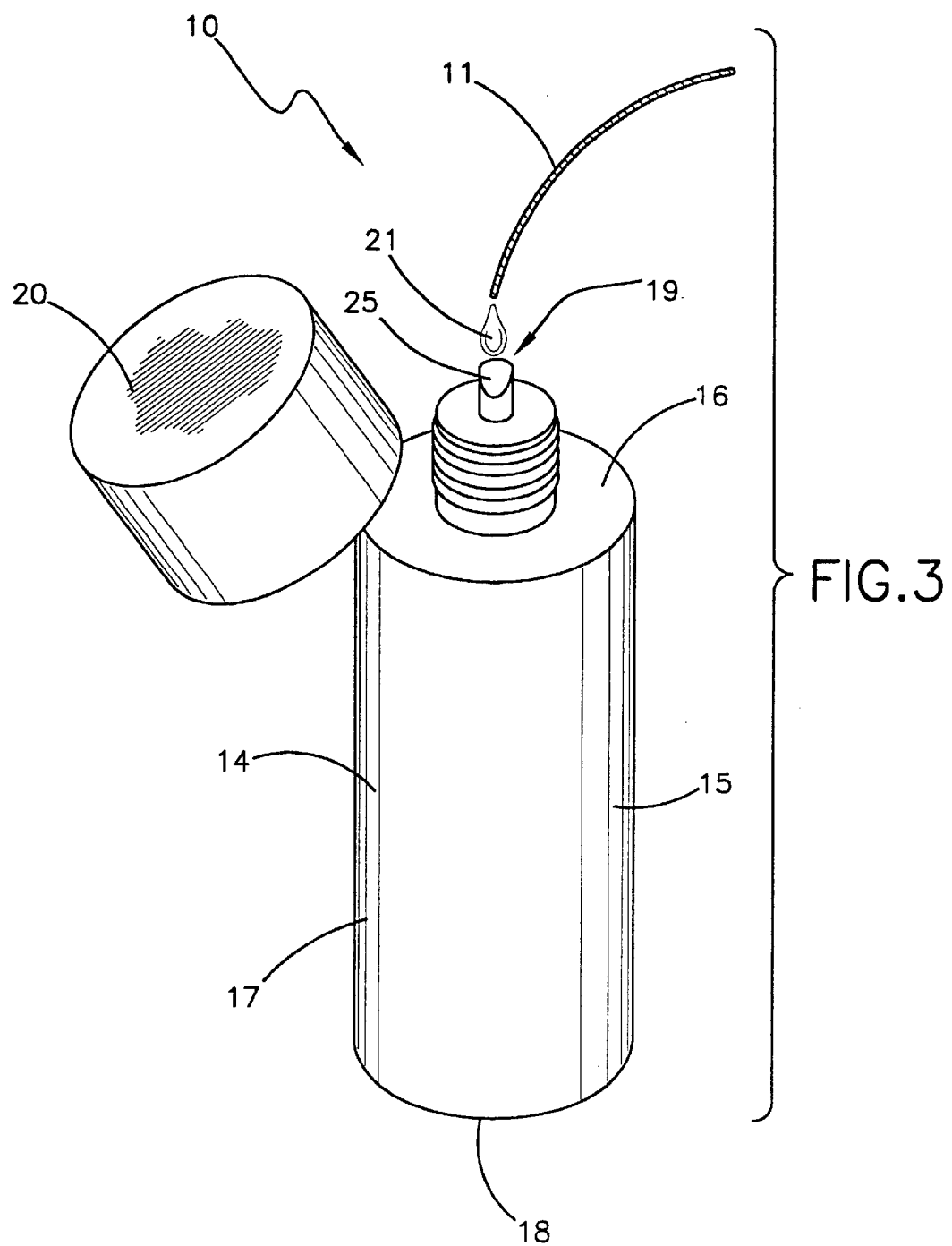

CLEANING KIT FOR OLD PIERCED HOLES IN A PERSON'S BODY

BACKGROUND OF THE INVENTION

1. Field of the Invention

The present invention relates to a pierced hole cleaning kit and more particularly pertains to a new cleaning kit for old pierced holes in a person's body for cleaning and sanitizing pierced holes of a person's body.

2. Description of the Prior Art

The use of a pierced hole cleaning kit is known in the prior art. More specifically, a pierced hole cleaning kit heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,636,203; U.S. Pat. No. 4,497,402; U.S. Pat. No. 4,798,216; U.S. Pat. No. 5,183,461; U.S. Pat. No. 5,739,168; U.S. Pat. No. Des. 346,443; and U.S. Pat. No. Des. 401,326.

While these devices fulfill their respective, particular objectives and requirements, the aforementioned patents do not disclose a new cleaning kit for old pierced holes in a person's body. The inventive device includes a plurality of elongate flexible cleaning members being adapted to pass through pierced holes of a person's body; and also includes a packet member for storing the elongate flexible cleaning members therein; and further includes a container of cleaning solution with the cleaning solution being disposable upon the elongate flexible cleaning members.

In these respects the cleaning kit for old pierced holes in a person's body according to the present invention substantially departs from the conventional concepts and designs of the prior art, and in so doing provides an apparatus primarily developed for the purpose of cleaning and sanitizing pierced holes of a person's body.

SUMMARY OF THE INVENTION

In view of the foregoing disadvantages inherent in the known types of pierced hole cleaning kit now present in the prior art, the present invention provides a new cleaning kit for old pierced holes in a person's body construction wherein the same can be utilized for cleaning and sanitizing pierced holes of a person's body.

The general purpose of the present invention, which will be described subsequently in greater detail, is to provide a new cleaning kit for old pierced holes in a person's body which has many of the advantages of the pierced hole cleaning kit mentioned heretofore and many novel features that result in a new cleaning kit for old pierced holes in a person's body which is not anticipated, rendered obvious, suggested, or even implied by any of the prior art pierced hole cleaning kit, either alone or in any combination thereof.

To attain this, the present invention generally comprises a plurality of elongate flexible cleaning members being adapted to pass through pierced holes of a person's body; and also includes a packet member for storing the elongate flexible cleaning members therein; and further includes a container of cleaning solution with the cleaning solution being disposable upon the elongate flexible cleaning members.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new cleaning kit for old pierced holes in a person's body which has many of the advantages of the pierced hole cleaning kit mentioned heretofore and many novel features that result in a new cleaning kit for old pierced holes in a person's body which is not anticipated, rendered obvious, suggested, or even implied by any of the prior art pierced hole cleaning kit, either alone or in any combination thereof.

It is another object of the present invention to provide a new cleaning kit for old pierced holes in a person's body which may be easily and efficiently manufactured and marketed.

It is a further object of the present invention to provide a new cleaning kit for old pierced holes in a person's body which is of a durable and reliable construction.

An even further object of the present invention is to provide a new cleaning kit for old pierced holes in a person's body which is susceptible of a low cost of manufacture with regard to both materials and labor, and which accordingly is then susceptible of low prices of sale to the consuming public, thereby making such cleaning kit for old pierced holes in a person's body economically available to the buying public.

Still yet another object of the present invention is to provide a new cleaning kit for old pierced holes in a person's body which provides in the apparatuses and methods of the prior art some of the advantages thereof, while simultaneously overcoming some of the disadvantages normally associated therewith.

Still another object of the present invention is to provide a new cleaning kit for old pierced holes in a person's body for cleaning and sanitizing pierced holes of a person's body.

Yet another object of the present invention is to provide a new cleaning kit for old pierced holes in a person's body which includes a plurality of elongate flexible cleaning members being adapted to pass through pierced holes of a person's body; and also includes a packet member for storing the elongate flexible cleaning members therein; and further includes a container of cleaning solution with the cleaning solution being disposable upon the elongate flexible cleaning members.

Still yet another object of the present invention is to provide a new cleaning kit for old pierced holes in a person's,body that is easy and convenient to use and apply to the pierced holes in one's body.

Even still another object of the present invention is to provide a new cleaning kit for old pierced holes in a person's body that effectively eliminates irritations and prevents infections to the pierced holes.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an exploded perspective view of the present invention.

DESCRIPTION OF THE PREFERRED EMBODIMENT

Figure 1:
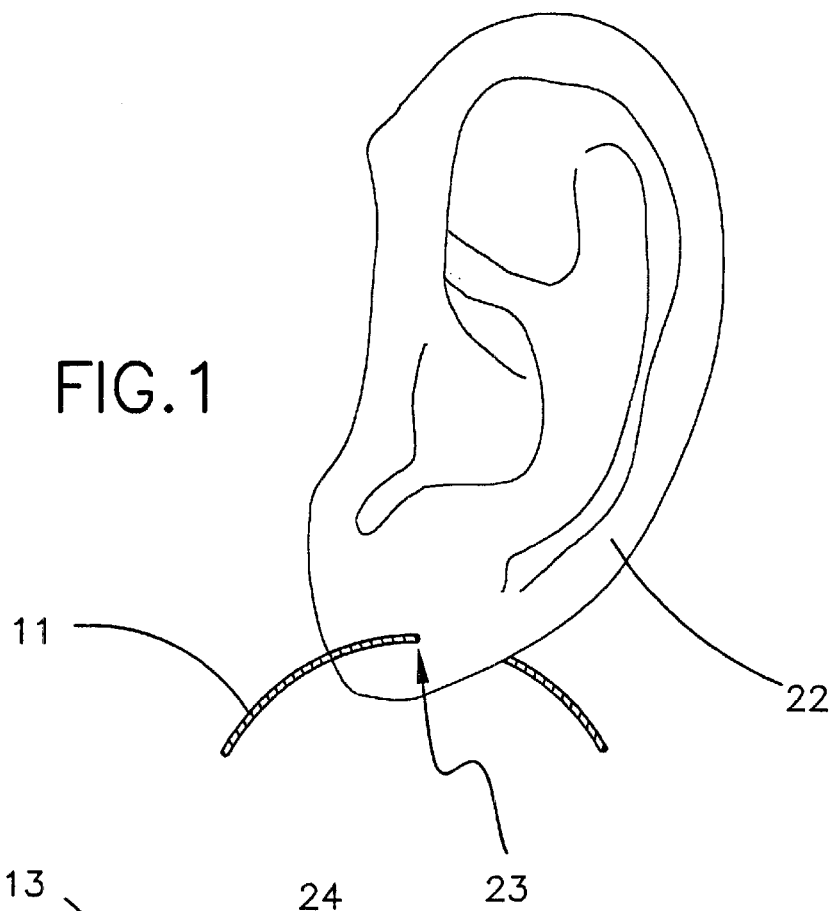
FIG. 1 is a perspective view of an elongate flexible cleaning member of a new cleaning kit for old pierced holes in a person's body according to the present invention and shown in use.
Figure 2:
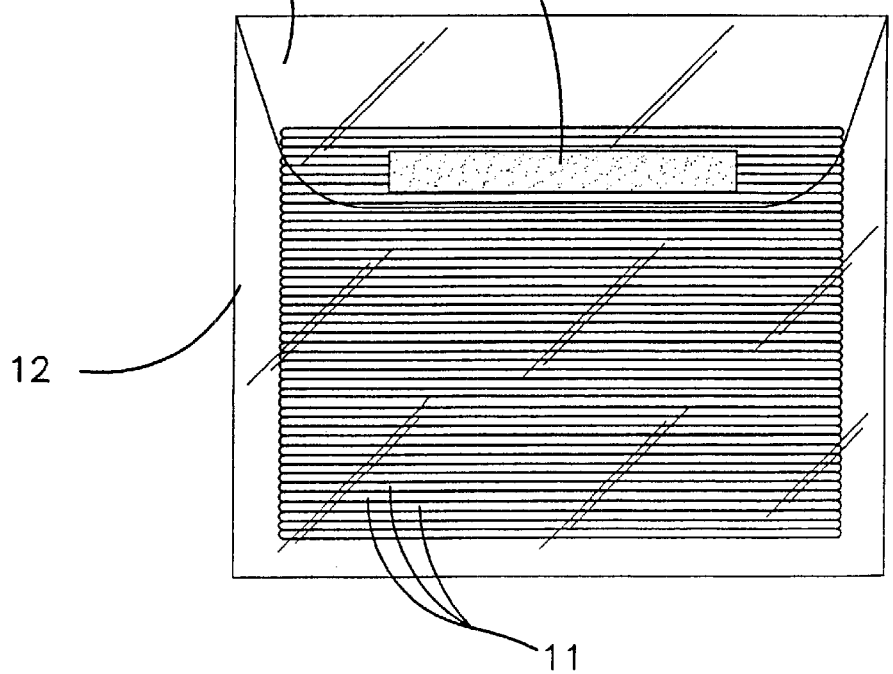
FIG. 2 is a side elevational view of a packet of elongate flexible cleaning members of the present invention.

With reference now to the drawings, and in particular to FIGS. 1 through 3 thereof, a new cleaning kit for old pierced holes in a person's body embodying the principles and concepts of the present invention and generally designated by the reference numeral 10 will be described.

As best illustrated in FIGS. 1 through 3, the cleaning kit for old pierced holes in a person's body 10 generally comprises a plurality of elongate flexible cleaning members 11 being adapted to pass through pierced holes 23 of a person's body 22. Each of the elongate flexible cleaning members 11 is generally a stick-like member 11 being made of cotton material and having a plastic coating thereabout and also having a light blue colored tip and being adapted to be in contact with the edges forming the pierced holes 23.

A packet member 12,13 for storing the elongate flexible cleaning members 11 is generally a bag 12 having a closable flap 13 for closing the bag 12 and further having strips of hook and loop fasteners 24 conventionally attached to the flap 13 and to the bag 12. A two fluid ounce container 14 of cleaning solution 21 with the cleaning solution 21 being disposable and dispensable upon the elongate flexible cleaning members 11. The two fluid ounce container 14 includes a tubular member 15 having side, bottom, and top walls 17–18, and also having a dispensing hole 19 being conventionally disposed through the top wall 16 and further having an absorbing piece of material 25 such as a sponge being attached to said container and being disposed over the dispensing hole for absorbing the cleaning solution and evenly applying the cleaning solution to the elongate flexible cleaning members 11, and also includes a cap member 20 being removably attached upon a top of the tubular member 15 and closable over the dispensing hole 19. The cleaning solution 21 includes purified water and Benzal Konium Chloride of approximately 0.06 percent, and is adapted to clean about edges forming the pierced holes 23.

In use, the user puts the cleaning solution 21 upon and about one of the elongate flexible cleaning members 11 and passes the elongate flexible cleaning member 11 through the pierced hole 23 to be cleaned.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A cleaning kit for old pierced holes in a person's body comprising:

a plurality of elongate flexible cleaning members being adapted to pass through pierced holes of a person's body, wherein each of said elongate flexible cleaning members is generally a stick-like member being made of cotton material, and has a plastic coating thereabout, and also has a colored tip, and is adapted to be in contact with the edges forming the pierced holes;

a packet member for storing said elongate flexible cleaning members; and a two fluid ounce container of cleaning solution with said cleaning solution being disposable upon said elongate flexible cleaning members.

2. A cleaning kit for old pierced holes in a person's body as described in claim 1, wherein said packet member is generally a bag having a closable flap for closing said bag and further having strips of hook and loop fasteners conventionally attached to said flap and to said bag.

3. A cleaning kit for old pierced holes in a person's body as described in claim 1, wherein said container includes a tubular member having side, bottom, and top walls, and also having a dispensing hole being disposed through said top wall and further having an absorbing piece of material being attached to said container and being disposed over said hole for absorbing the cleaning solution and evenly applying the cleaning solution to said elongate flexible cleaning members, and also includes a cap member being removably attached upon a top of said tubular member and closable over said dispensing hole.

4. A cleaning kit for old pierced holes in a person's body as described in claim 3, wherein said cleaning solution includes purified water and Benzalkonium Chloride of approximately 0.06 percent, and is adapted to clean about edges forming the pierced holes.

5. A cleaning kit for old pierced holes in a person's body comprising:

a plurality of elongate flexible cleaning members being adapted to pass through pierced holes of a person's body, each of said elongate flexible cleaning members being generally a stick-like member being made of cotton material, and having a plastic coating thereabout, and also having a colored tip, and being adapted to be in contact with the edges forming the pierced holes;

a packet member for storing said elongate flexible cleaning members, said packet member being generally a bag having a closable flap for closing said bag and further having strips of hook and loop fasteners conventionally attached to said flap and to said bag; and a two fluid ounce container of cleaning solution with said cleaning solution being disposable upon said elongate flexible cleaning members, said container including a tubular member having side, bottom, and top walls, and also having a dispensing hole being disposed through said top wall and further having an absorbing piece of material being attached to said container and being disposed over said dispensing hole for absorbing the cleaning solution and evenly applying the cleaning solution to said elongate flexible cleaning members, and also including a cap member being removably attached upon a top of said tubular member and closable over said dispensing hole, said cleaning solution including purified water and Benzalkonium Chloride of approximately 0.06 percent, and being adapted to clean about edges forming the pierced holes.

* * * * *